US009174929B2

(12) United States Patent
Thetford et al.

(10) Patent No.: US 9,174,929 B2
(45) Date of Patent: *Nov. 3, 2015

(54) DISPERSANT COMPOSITION

(71) Applicant: Lubrizol Advanced Materials, Inc., Cleveland, OH (US)

(72) Inventors: Dean Thetford, Norden (GB); Matthew D. Gieselman, Willoughby Hills, OH (US); Joanne L. Jones, Nottingham (GB)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 248 days.

This patent is subject to a terminal disclaimer.

(21) Appl. No.: 13/678,651

(22) Filed: Nov. 16, 2012

(65) Prior Publication Data

US 2013/0072704 A1 Mar. 21, 2013

Related U.S. Application Data

(63) Continuation of application No. PCT/US2011/036622, filed on May 16, 2011.

(60) Provisional application No. 61/346,556, filed on May 20, 2010.

(51) Int. Cl.
| | | |
|---|---|---|
| *C07C 211/00* | (2006.01) |
| *C08G 18/42* | (2006.01) |
| *C08G 69/26* | (2006.01) |
| *C08L 77/00* | (2006.01) |
| *C08L 79/00* | (2006.01) |
| *C07C 229/30* | (2006.01) |
| *C09D 7/02* | (2006.01) |
| *C09D 11/03* | (2014.01) |
| *C09D 11/36* | (2014.01) |

(52) U.S. Cl.
CPC ............ *C07C 229/30* (2013.01); *C09D 7/02* (2013.01); *C09D 11/03* (2013.01); *C09D 11/36* (2013.01)

(58) Field of Classification Search
CPC ..................................... C07C 229/30
See application file for complete search history.

(56) References Cited

U.S. PATENT DOCUMENTS

| 4,224,212 | A | 9/1980 | Topham | |
|---|---|---|---|---|
| 8,557,753 | B2 * | 10/2013 | Gieselman et al. | 508/454 |
| 8,569,217 | B2 * | 10/2013 | Gieselman et al. | 508/543 |
| 8,809,443 | B2 * | 8/2014 | Thetford et al. | 524/539 |

FOREIGN PATENT DOCUMENTS

| EP | 1574559 A1 | 9/2005 |
|---|---|---|
| GB | 1373660 A | 11/1974 |
| WO | 02072639 A2 | 9/2002 |
| WO | 2006138269 A2 | 12/2006 |
| WO | 2010062842 A1 | 11/2009 |

* cited by examiner

*Primary Examiner* — Clinton Brooks
(74) *Attorney, Agent, or Firm* — Samuel B. Laferty; Teresan W. Gilbert

(57) ABSTRACT

The present invention relates to a composition containing a particulate solid, a non-polar organic medium, and a compound obtained/obtainable by reacting an aromatic amine with hydrocarbyl-substituted acylating agent, wherein the hydrocarbyl-substituted acylating agent is selected from the group consisting of an oligomer or polymer from condensation polymerization of a hydroxy-substituted $C_{10\text{-}30}$ carboxylic acid into a polyester, an optionally hydroxy-substituted $C_{10\text{-}30}$ carboxylic acid, a $C_{10\text{-}30}$-hydrocarbyl substituted acylating agent, and a polyolefin-substituted maleic anhydride. The invention further provides compositions for inks, thermoplastics, plasticizers, plastisols, crude grinding and flush.

10 Claims, No Drawings

DISPERSANT COMPOSITION

CROSS REFERENCE TO RELATED APPLICATION

This application is a continuation of International Application Serial No. PCT/US2011/036,622 filed on May 16, 2011, which claims the benefit of U.S. Provisional Application No. 61/346,556 filed on May 20, 2010.

FIELD OF INVENTION

The present invention relates to a composition containing a particulate solid, a non-polar organic medium, and a compound obtained/obtainable by reacting an aromatic amine with hydrocarbyl-substituted acylating agent. The invention further provides compositions for coatings, inks, toners, plastic materials (such as thermoplastics), plasticisers, plastisols, crude grinding and flush.

BACKGROUND OF THE INVENTION

Many formulations such as inks, paints, mill-bases and plastics materials require effective dispersants for uniformly distributing a particulate solid in a non-polar organic medium.

Numerous publications disclose polyester amine dispersants derived from a poly($C_{2-4}$-alkylene imine) such as polyethylene imine to which is attached a polyester chain. The polyester chain may be derived from 12-hydroxy stearic acid, as disclosed in U.S. Pat. No. 4,224,212, or it may be derived from two or more different hydroxy carboxylic acids. GB 1 373 660 discloses polyester amine dispersants obtainable by reaction of a polyester from hydroxycarboxylic acid with diamine, especially alkylene diamines and salts thereof.

SUMMARY OF THE INVENTION

One objective of the present invention is to provide compounds that are capable of at least one of improving colour strength, increasing a particulate solid load, forming improved dispersions, having improved brightness, and producing a composition with reduced viscosity.

In one embodiment, the invention provides a composition comprising a particulate solid, a non-polar organic medium, and a compound obtained/obtainable by reacting an aromatic amine with a hydrocarbyl-substituted acylating agent, wherein the hydrocarbyl-substituted acylating agent is selected from the group consisting of an oligomer or polymer from condensation polymerization of a hydroxy-substituted $C_{10-30}$ carboxylic acid into a polyester, an optionally hydroxy-substituted $C_{10-30}$ carboxylic acid, a $C_{10-30}$-hydrocarbyl substituted acylating agent, and a polyolefin-substituted acylating agent (typically succinic anhydride).

The compound may have a number average molecular weight of 500 to 20,000, or 600 to 15,000, or 700 to 5000.

The aromatic amine may be mono-functional when reacting with the hydrocarbyl-substituted acylating agent but typically di- or poly-functional.

In one embodiment, the aromatic amine to hydrocarbyl-substituted acylating agent mole ratio may be in the range of 2:1 to 1:10, or 2:1 to 1:4, or 1:1 to 1:3, or 1:1 to 1:2, or 1:2.

The hydrocarbyl-substituted acylating agent may be at least 50 mol %, or at least 75 mol %, or at least 90 mol % mono-functional or di-functional (when in the form of an anhydride) when reacted with the aromatic amine.

The particulate solid may be a pigment or a filler.

The non-polar organic medium may, for instance, include a mineral oil, an aliphatic hydrocarbon, an aromatic hydrocarbon, a plastic material (typically a thermoplastic resin), or a plasticiser.

The present invention also provides a composition comprising a particulate solid (typically a pigment or filler), a non-polar organic medium and a compound of the invention described above.

In one embodiment, the invention provides a paint or ink comprising a particulate solid, a non-polar organic medium, a film-forming resin and a compound of the invention disclosed herein.

The ink may be an ink-jet ink, a gravure ink, or an offset ink.

In one embodiment, the invention provides a composition comprising a compound of the present invention, a particulate solid (typically a pigment or filler), and a non-polar organic medium, wherein the organic medium may be a plastics material. The plastic material may be a thermoplastic resin.

In one embodiment, the invention provides for the use of the compound described herein as a dispersant in a composition disclosed herein.

In one embodiment, the invention provides a compound obtained/obtainable by reacting an aromatic amine with a hydrocarbyl-substituted acylating agent, wherein the hydrocarbyl-substituted acylating agent is selected from the group consisting of an oligomer or polymer from condensation polymerisation of a hydroxy-substituted $C_{10-30}$ carboxylic acid into a polyester, and an optionally hydroxy-substituted $C_{10-30}$ carboxylic acid, or mixtures thereof.

DETAILED DESCRIPTION OF THE INVENTION

The present invention provides a composition and use disclosed herein above.

Aromatic Amine

The aromatic amine includes aniline, nitroaniline, aminocarbazole, 4-aminodiphenylamine (ADPA), and coupling products of ADPA. In one embodiment, the amine may be 4-aminodiphenylamine (ADPA), or coupling products of ADPA. In one embodiment, the amine may be coupling products of ADPA. In one embodiment, the aromatic amine may not be a heterocycle.

Coupled products of ADPA may be represented by the formula (1):

Formula (1)

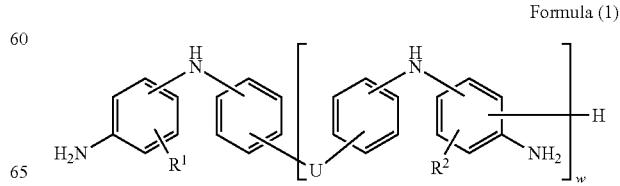

wherein independently each variable, $R^1$ may be hydrogen or a $C_{1-5}$ alkyl group (typically hydrogen);

$R^2$ may be hydrogen or a $C_{1-5}$ alkyl group (typically hydrogen);

U may be an aliphatic, alicyclic or aromatic group, with the proviso that when U is aliphatic, the aliphatic group may be linear or branched alkylene group containing 1 to 5, or 1 to 2 carbon atoms; and w may be 1 to 10, or 1 to 4, or 1 to 2 (typically 1).

In one embodiment, the coupled ADPA of Formula (1) may be represented by Formula (1a):

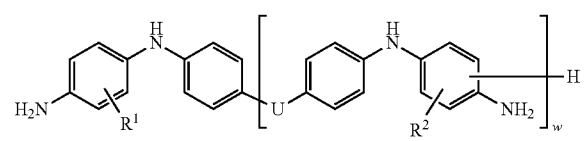

Formula (1a)

wherein independently each variable, $R^1$ may be hydrogen or a $C_{1-5}$ alkyl group (typically hydrogen);

$R^2$ may be hydrogen or a $C_{1-5}$ alkyl group (typically hydrogen);

U may be an aliphatic, alicyclic or aromatic group, with the proviso that when U is aliphatic, the aliphatic group may be linear or branched alkylene group containing 1 to 5, or 1 to 2 carbon atoms; and w may be 1 to 10, or 1 to 4, or 1 to 2 (typically 1).

Alternatively, the compound of Formula (1a) may also be represented by:

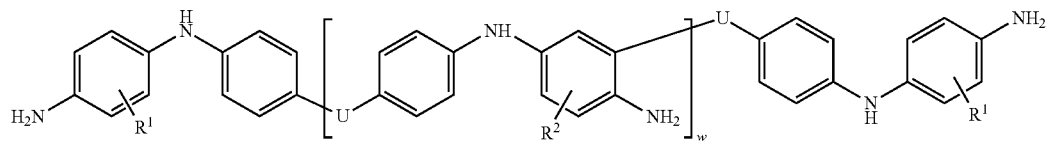

wherein each variable U, $R^1$, and $R^2$ are the same as described above and w is 0 to 9 or 0 to 3 or 0 to 1 (typically 0).

Examples of an amine having at least 3 aromatic groups may be represented by any of the following Formulae (2) and/or (3):

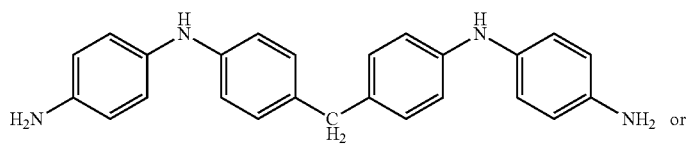

Formula (2)

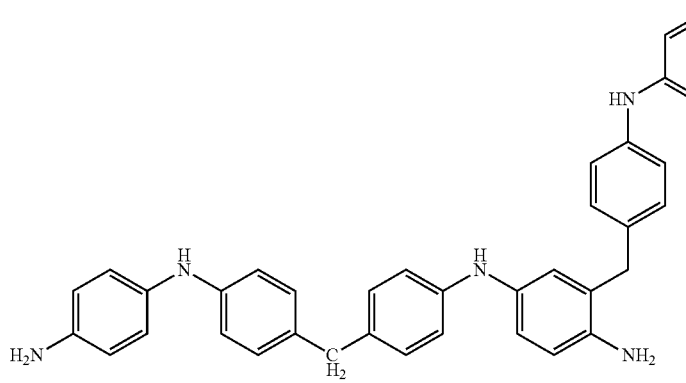

Formula (3)

A person skilled in the art will appreciate that compounds of Formulae (2) and (3) may also react with the aldehyde described below to form acridine derivatives. Acridine derivatives that may be formed include compounds represented by Formula (2a) or (3a) below. In addition to these compounds representing these formulae, a person skilled in the art will also appreciate that other acridine structures may be possible where the aldehyde reacts with other benzyl groups bridged with the >NH group. Examples of acridine structures include those represented by Formulae (2a) and (3a):

hyde may be aliphatic, alicyclic or aromatic. The aliphatic aldehyde may be linear or branched. Examples of a suitable aromatic aldehyde include benzaldehyde or o-vanillin. Examples of an aliphatic aldehyde include formaldehyde (or a reactive equivalent thereof such as formalin or paraformaldehyde), ethanal or propanal. Typically, the aldehyde may be formaldehyde or benzaldehyde.

The acylating agent, from which the compound of the invention may be derivable, may have one or more acid func- Formula (2a)

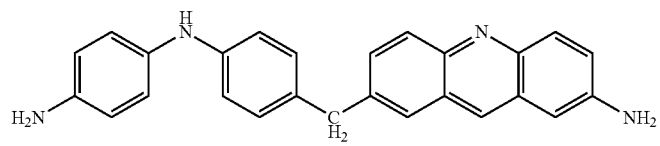

Formula (3a)

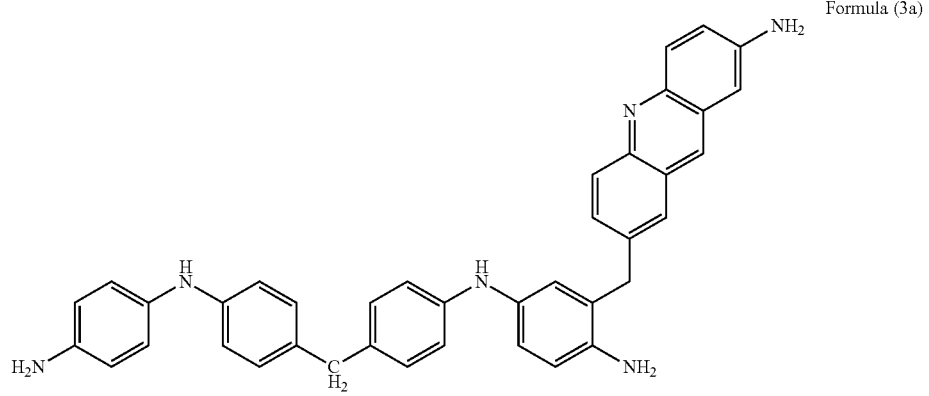

Any or all of the N-bridged aromatic rings are capable of such further condensation and perhaps aromatisation. One other of many possible structures is shown in Formula (3b):

tional groups, such as a carboxylic acid or anhydride thereof. Examples of an acylating agent include an alpha, beta-unsaturated mono- or polycarboxylic acid, anhydride ester or Formula (3b)

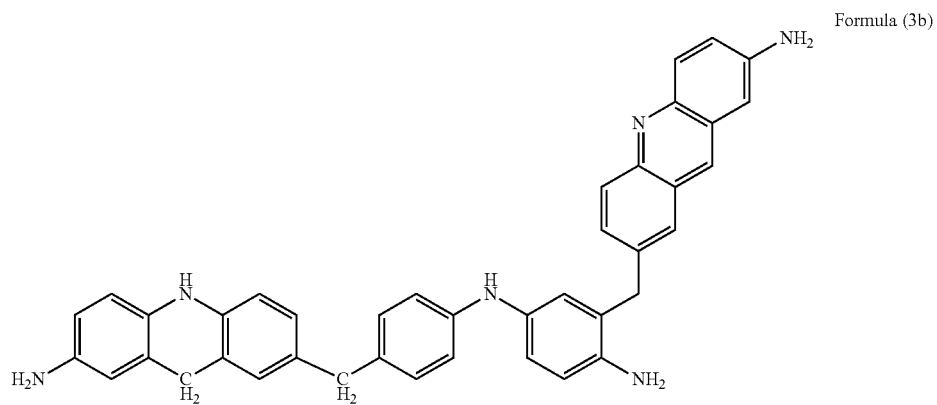 [SMILES: Nc1ccc2c(c1)Cc1cc(Cc3ccc(Nc4ccc(N)c(Cc5ccc6nc7ccc(N)cc7cc6c5)c4)cc3)ccc1N2]

Examples of the coupled ADPA include bis[p-(p-aminoanilino)phenyl]-methane, 2-(7-amino-acridin-2-ylmethyl)-N-4-{4-[4-(4-amino-phenylamino)-benzyl]-phenyl}-benzene-1,4-diamine, $N^4$-{4-[4-(4-amino-phenylamino)-benzyl]-phenyl}-2-[4-(4-amino-phenylamino)-cyclohexa-1,5-dienylmethyl]-benzene-1,4-diamine, N-[4-(7-amino-acridin-2-ylmethyl)-phenyl]-benzene-1,4-diamine, or mixtures thereof.

The coupled ADPA may be prepared by a process comprising reacting the aromatic amine with an aldehyde. The aldederivative thereof. Examples of an acylating agent include (meth)acrylic acid, methyl(meth)acrylate, maleic acid or anhydride, fumaric acid, itaconic acid or anhydride, or mixtures thereof. In one embodiment, the acylating agent, from which the compound of the invention may be derivable may, be maleic anhydride, or mixtures thereof.

In one embodiment, the compound of the invention may be obtained/obtainable by reacting an aromatic amine with a hydroxy-substituted $C_{10-30}$ carboxylic acid, or mixtures thereof.

The hydroxy-substituted $C_{10-30}$ carboxylic acid may typically be polymerised to form a polyester. The polyester may be a polymerisation product of a hydroxy-substituted carboxylic acid of general formula HO—X—COOH, wherein X is a divalent saturated or unsaturated aliphatic radical containing at least 4 carbon atoms between the hydroxyl and carboxylic acid groups. The hydroxy-substituted $C_{10-30}$ carboxylic acid may also be in a mixture with a $C_{10-30}$ carboxylic acid that is free from hydroxyl groups.

X may contain 12-20 carbon atoms; and that there are between 3 and 14, or 8 and 14 carbon atoms between the carboxylic acid and hydroxy groups.

Examples of the hydroxy-substituted $C_{10-30}$ carboxylic acid may include ricinoleic acid, 12-hydroxystearic acid, a mixture of 9- and 10-hydroxystearic acids, 10-hydroxyundecanoic acid, 12-hydroxydodecanoic acid, 4-hydroxydecanoic acid, 5-hydroxydecanoic acid (or delta-decanolactone), or 5-hydroxydodecanoic acid (or delta dodecanolactone). In different embodiments, the hydroxy-substituted $C_{10-30}$ carboxylic acid may be ricinoleic acid, 12-hydroxystearic acid, or a mixture of 9- and 10-hydroxystearic acids. In one embodiment, the hydroxy-substituted $C_{10-30}$ carboxylic acid may be a mixture of ricinoleic acid and either 12-hydroxystearic acid or 9- and 10-hydroxystearic acids.

The polyester may have 4 to 20 repeat units of the hydroxy-substituted $C_{10-30}$ carboxylic acid.

The polyester may be a homopolymer or a copolymer. The copolymer may be either a random or block copolymer.

In one embodiment, the compound of the invention may be obtained/obtainable by reacting an aromatic amine with an optionally hydroxy-substituted $C_{10-30}$ carboxylic acid (typically a $C_{10-30}$ carboxylic acid), or mixtures thereof.

The optionally hydroxy-substituted $C_{10-30}$ carboxylic acid may include ricinoleic acid, 12-hydroxystearic acid, capric acid, lauric acid, myristic acid, palmitic acid, stearic acid, behenic acid, oleic acid, or mixtures thereof. In one embodiment, the $C_{10-30}$ carboxylic acid may include lauric acid or stearic acid. In one embodiment, the optionally hydroxy-substituted $C_{10-30}$ carboxylic acid may include a mixture of (i) at least one of ricinoleic acid, or 12-hydroxystearic acid, and (ii) at least one of $C_{10-30}$ carboxylic acid such as lauric acid or stearic acid.

In one embodiment, the compound of the invention may be obtained/obtainable by reacting one mole of an aromatic amine with a one to two moles of a $C_{10-30}$ carboxylic acid, or mixtures thereof. The compound may be particularly useful in a composition including a plastic material.

In one embodiment, the compound of the invention may be obtained/obtainable by reacting an aromatic amine with a mixture of (i) $C_{10-30}$-hydrocarbyl substituted acylating agent (as described above), and (ii) a hydroxy-substituted $C_{10-30}$ carboxylic acid (as described above). In one embodiment, the mixture includes (i) stearic acid, and (ii) a polyester of hydroxystearic acid or a polyester of ricinoleic acid.

In one embodiment, the compound of the invention may be obtained/obtainable by reacting an aromatic amine with a $C_{10-30}$-hydrocarbyl substituted acylating agent, or mixtures thereof.

The $C_{10-30}$-hydrocarbyl substituted acylating agent may be an alk(en)yl-substituted succinic acid, anhydride, or partial esters thereof. Examples of suitable succinic anhydrides include dodecyl succinic anhydride, hexadecyl succinic anhydride, octadecyl succinic anhydride, eicosyl succinic anhydride, $C_{24-28}$-alkyl succinic anhydride, dodecenyl succinic anhydride, hexadecenyl succinic anhydride, octadecenyl succinic anhydride, eicosenyl succinic anhydride, $C_{24-28}$-alkenyl succinic anhydride, or mixtures thereof. In one embodiment, the $C_{10-30}$-hydrocarbyl substituted acylating agent may be hexadecyl succinic anhydride, octadecyl succinic anhydride, or mixtures thereof.

In one embodiment, the compound of the invention may be obtained/obtainable by reacting an aromatic amine with a polyolefin-substituted succinic anhydride, or mixtures thereof.

The polyolefin-substituted succinic anhydride may be a polyisobutylene succinic anhydride. The polyisobutylene from which the polyisobutylene succinic anhydride is derivable may have a number average molecular weight of 300 to 5000, 450 to 4000, 500 to 3000 or 550 to 2500. Particular ranges of the number average molecular weight may include 550 to 1000, or 750 to 1000, or 950 to 1000, or 1600 to about 2300.

The polyolefin may have a vinylidene group. The vinylidene group may be present on at least 2 wt. %, or at least 40%, or at least 50%, or at least 60%, or at least 70% of the polyolefin molecules. Often, the amount of vinylidene group present is about 75%, about 80% or about 85%.

When the polyolefin is a polyisobutylene the polyolefin may be obtained commercially under the tradenames of Glissopal®1000 or Glissopal®2300 (commercially available from BASF), TPC®555, TPC®575 or TPC®595 (commercially available from Texas Petrochemicals).

The polyolefin-substituted succinic anhydride may be obtained by reacting a polyolefin (typically polyisobutylene) with maleic anhydride by Diels Alder or by an "ene" reaction. Both reactions are known in the art. In one embodiment, the polyolefin-substituted succinic anhydride may be obtained by reacting a polyolefin (typically polyisobutylene) with maleic anhydride by an "ene" reaction.

The compound of the invention may be prepared by reacting an aromatic amine with a hydrocarbyl-substituted acylating agent at a reaction temperature in the range of 80° C. to 220° C., or 100° C. to 200° C.

In one embodiment, the aromatic amine to hydrocarbyl-substituted acylating agent mole ratio may be in the range of 2:1 to 1:10, or 2:1 to 1:4, or 1:1 to 1:3, or 1:1 to 1:2, or 1:2. In one embodiment, the aromatic amine to hydrocarbyl-substituted acylating agent mole ratio may be 1:1 to 1:2, or 1:2.

The reaction may be carried out in an inert atmosphere, for example, under nitrogen or argon, typically nitrogen.

The reaction may be a one-step process or a two-step process.

A two-step process may be employed if the hydrocarbyl-substituted acylating agent is a polyester. The first step comprises forming a polyester by copolymerising a hydroxy-substituted $C_{10-30}$ carboxylic acid as described above. The reaction may also optionally be carried out in the presence of a catalyst such as zirconium butoxide. The polymerisation step is known and is described for instance in U.S. Pat. No. 3,996,059. The second step comprises reacting the polyester with the aromatic amine.

Processes to prepare the compound of the invention when the hydrocarbyl-substituted acylating agent is a polyolefin-substituted acylating agent is described in International Application U.S. Ser. No. 09/065,452 (filed 23 Nov. 2009), also provisionally filed with U.S. Patent Application No. 61/118,012 (on 26 Nov. 2008). A process to prepare a compound of this type is shown below in EX1 and EX2.

Preparative Example 1 (EX1) is a coupled aromatic amine head group synthesis. 500 mL of 2M hydrochloric acid is added to a one-liter 4-neck flask equipped with an overhead stirrer, thermowell, addition funnel with nitrogen line, and condenser. 184.2 g of 4-aminodiphenylamine is added, and the flask is heated to 75° C. The addition funnel is then charged with 40.5 g of a 37% formaldehyde solution and the solution is added drop-wise to the flask over a period of 30 minutes. The flask is maintained at 100° C. for 4 hours. The flask is then cooled to ambient temperature. 80 g of a 50/50 wt./wt. solution of sodium hydroxide in water is added over 30 minutes. At the end of the reaction, a solid product is obtained via filtration. The resultant solid product is believed to primarily be the compound of Formula (2) as described above. In addition, the resultant product may contain a small percentage of product based on Formula (3) as described above.

Preparative Example 2 (EX2) is a reaction product of polyisobutylene succinic anhydride with the product of EX1. A three-liter, 4-neck flask equipped with an overhead stirrer, thermowell, subsurface inlet with nitrogen line, and Dean-Stark trap with condenser is charged with polyisobutylene succinic anhydride (1270.0 g) (where the polyisobutylene from which it is derived has a number average molecular weight of 2000) and diluent oil (1400.1 g). The flask is heated to 90° C. The product of EX1 (442.0 g) is added slowly. The temperature is then raised to 110° C. and held until the water from reaction with the product of EX1 is removed. The temperature is then raised to 160° C. and held for 10 hours. To the flask is added a portion of a diatomaceous earth filter aid, and then flask contents are filtered through a second portion of the diatomaceous earth filter aid. The resultant product is a dark oil with a nitrogen content of 0.65 wt. %.

INDUSTRIAL APPLICATION

In one embodiment, the compound of the invention disclosed herein may be a dispersant, typically used for dispersing particulate solid materials.

The compound of the invention disclosed herein in different embodiments may be present in the composition of the invention in a range selected from 0.1 to 50 wt. %, or 0.25 to 35 wt. %, and 0.5 to 30 wt. %.

The particulate solid present in the composition may be any inorganic or organic solid material which is substantially insoluble in the non-polar organic medium at the temperature concerned and which it is desired to stabilize in a finely divided form therein. The particulate solids may be in the form of a granular material, a fibre, a platelet or in the form of a powder, often a blown powder. In one embodiment, the particulate solid is a pigment of a filler. The pigment may be a organic or inorganic pigment, typically an organic pigment.

Examples of suitable particulate solids include pigments for solvent inks; pigments, extenders, fillers, blowing agents and flame retardants for paints and plastics materials; dyes, especially disperse dyes; optical brightening agents and textile auxiliaries for solvent dyebaths, inks and other solvent application systems; solids for oil-based and inverse-emulsion drilling muds; metals; particulate ceramic materials and magnetic materials for ceramics, piezoceramic printing, refactories, abrasives, foundry, capacitors, fuel cells, ferrofluids, conductive inks, magnetic recording media, water treatment and hydrocarbon soil remediation; organic and inorganic nanodisperse solids, such as metal, metal oxides and carbon for electrodes in batteries; fibres such as carbon and boron for composite materials; and biocides, agrochemicals and pharmaceuticals which are applied as dispersions in organic media.

In one embodiment, the particulate solid may be an organic pigment from any of the recognised classes of pigments described, for example, in the Third Edition of the Colour Index (1971) and subsequent revisions of, and supplements thereto, under the chapter headed "Pigments". Examples of organic pigments are those from the azo, disazo, trisazo, condensed azo, azo lakes, naphthol pigments, anthanthrone, anthrapyrimidine, anthraquinone, benzimidazolone, carbazole, diketopyrrolopyrrole, flavanthrone, indigoid pigments, indanthrone, isodibenzanthrone, isoindanthrone, isoindolinone, isoindoline, isoviolanthrone, metal complex pigments, oxazine, perylene, perinone, pyranthrone, pyrazoloquinazolone, quinacridone, quinophthalone, thioindigo, triarylcarbonium pigments, triphendioxazine, xanthene and phthalocyanine series, especially copper phthalocyanine and its nuclear halogenated derivatives, and also lakes of acid, basic and mordant dyes. Carbon black, although strictly inorganic, behaves more like an organic pigment in its dispersing properties. In one embodiment, the organic pigments are phthalocyanines, especially copper phthalocyanines, monoazos, disazos, indanthrones, anthranthrones, quinacridones, diketopyrrolopyrroles, perylenes and carbon black including single- and multi-walled carbon nanotubes, reinforcing and non-reinforcing carbon black, graphite, Buckminster fullerenes, asphaltene, and graphene.

In one embodiment, the solid particulate is not carbon black, or has less than 80, 50, or 10 wt. % carbon and metal wear byproducts as a component of the particulate solid, based on the total weight of the solid particulate.

Other useful particulate solids include flame retardants such as pentabromodiphenyl ether, octabromodiphenyl ether, decabromodiphenyl ether, hexabromocyclododecane, ammonium polyphosphate, melamine, melamine cyanurate, antimony oxide and borates; biocides or industrial microbial agents such as those mentioned in Tables 2, 3, 4, 5, 6, 7, 8 and 9 of the chapter entitled "Industrial Microbial Agents" in Kirk-Othmer's Encyclopedia of Chemical Technology, Volume 13, 1981, $3^{rd}$ Edition, and agrochemicals such as the fungicides flutriafen, carbendazim, chlorothalonil and mancozeb.

The non-polar organic medium present in the composition of the invention in one embodiment may be a plastics material and in another embodiment an organic liquid.

In one embodiment, non-polar organic liquids are compounds containing aliphatic groups, aromatic groups or mixtures thereof. The non-polar organic liquids include non-halogenated aromatic hydrocarbons (e.g., toluene and xylene), halogenated aromatic hydrocarbons (e.g., chlorobenzene, dichlorobenzene, chlorotoluene), non-halogenated aliphatic hydrocarbons (e.g., linear and branched aliphatic hydrocarbons containing six or more carbon atoms both fully and partially saturated), halogenated aliphatic hydrocarbons (e.g., dichloromethane, carbon tetrachloride, chloroform, trichloroethane) and natural non-polar organics (e.g., vegetable oil, sunflower oil, linseed oil, terpenes and glycerides).

In one embodiment, the non-polar organic medium includes at least 0.1% by weight, or 1% by weight or more of a polar organic liquid based on the total organic liquid, with the proviso that the composition remains substantially non-polar. The non-polar medium may contain up to 5 wt. % or up to 10 wt. % of a polar organic liquid. Typically, the non-polar organic medium is substantially free of, to free of a polar organic liquid. In one embodiment, the non-polar medium is substantially free of, to free of water.

Examples of suitable polar organic liquids include amines, ethers, especially lower alkyl ethers, organic acids, esters, ketones, glycols, alcohols and amides. Numerous specific examples of such moderately strongly hydrogen bonding liquids are given in the book entitled "Compatibility and Solubility" by Ibert Mellan (published in 1968 by Noyes Development Corporation) in Table 2.14 on pages 39-40, and these liquids all fall within the scope of the term polar organic liquid as used herein.

In one embodiment, polar organic liquids include dialkyl ketones, alkyl esters of alkane carboxylic acids and alkanols, especially such liquids containing up to, and including, a total of 6 or 8 carbon atoms. As examples of the polar organic liquids include dialkyl and cycloalkyl ketones, such as acetone, methyl ethyl ketone, diethyl ketone, di-isopropyl ketone, methyl isobutyl ketone, di-isobutyl ketone, methyl isoamyl ketone, methyl n-amyl ketone and cyclohexanone; alkyl esters such as methyl acetate, ethyl acetate, isopropyl acetate, butyl acetate, ethyl formate, methyl propionate, methoxy propylacetate and ethyl butyrate; glycols and glycol esters and ethers, such as ethylene glycol, 2-ethoxyethanol, 3-methoxypropylpropanol, 3-ethoxypropylpropanol, 2-butoxyethyl acetate, 3-methoxypropyl acetate, 3-ethoxypropyl acetate and 2-ethoxyethyl acetate; alkanols such as methanol, ethanol, n-propanol, isopropanol, n-butanol and isobutanol and dialkyl and cyclic ethers such as diethyl ether and tetrahydrofuran. In one embodiment, solvents are alkanols, alkane carboxylic acids and esters of alkane carboxylic acids.

Examples of organic liquids, which may be used as polar organic liquids are film-forming resins. Examples of such film-forming resins include polyamides, such as Versamid™ and Wolfamid™, and cellulose ethers, such as ethyl cellulose and ethyl hydroxyethyl cellulose, nitrocellulose and cellulose acetate butyrate resins, including mixtures thereof. Examples of resins include short oil alkyd/melamine-formaldehyde, polyester/melamine-formaldehyde, thermosetting acrylic/melamine-formaldehyde, long oil alkyd, polyether polyols and multi-media resins, such as acrylic and urea/aldehyde.

The organic liquid may be a polyol, that is to say, an organic liquid with two or more hydroxy groups. In one embodiment, polyols include alpha-omega diols or alpha-omega diol ethoxylates.

If desired, the compositions containing a non-polar organic medium may contain other ingredients, for example, resins (where these do not already constitute the organic medium), binders, co-solvents, cross-linking agents, fluidising agents, wetting agents, anti-sedimentation agents, plasticisers, surfactants, dispersants other than the compound of the present invention, humectants, anti-foamers, anti-cratering agents, rheology modifiers, heat stabilizers, light stabilizers, UV absorbers, antioxidants, levelling agents, gloss modifiers, biocides and preservatives.

The plastics material may be a thermosetting resin or a thermoplastic resin. The thermosetting resins useful in this invention include resins which undergo a chemical reaction when heated, catalysed, or subject to ultra-violet, laser light, infra-red, cationic, electron beam, or microwave radiation and become relatively infusible. Typical reactions in thermosetting resins include oxidation of unsaturated double bonds, reactions involving epoxy/amine, epoxy/carbonyl, epoxy/hydroxyl, reaction of epoxy with a Lewis acid or Lewis base, polyisocyanate/hydroxy, amino resin/hydroxy moieties, free radical reactions or polyacrylate, cationic polymerization of epoxy resins and vinyl ether and condensation of silanol. Examples of unsaturated resins include polyester resins made by the reaction of one or more diacids or anhydrides with one or more diols. Such resins are commonly supplied as a mixture with a reactive monomer such as styrene or vinyltoluene and are often referred to as orthophthalic resins and isophthalic resins. Further examples include resins using dicyclopentadiene (DCPD) as a co-reactant in the polyester chain. Further examples also include the reaction products of bisphenol A diglycidyl ether with unsaturated carboxylic acids such as methacrylic acid, subsequently supplied as a solution in styrene, commonly referred to as vinyl ester resins.

Polymers with hydroxy functionality (frequently polyols) are widely used in thermosetting systems to crosslink with amino resins or polyisocyanates. The polyols include acrylic polyols, alkyd polyols, polyester polyols, polyether polyols and polyurethane polyols. Typical amino resins include melamine formaldehyde resins, benzoguanamine formaldehyde resins, urea formaldehyde resins and glycoluril formaldehyde resins. Polyisocyanates are resins with two or more isocyanate groups, including both monomeric aliphatic diisocyanates, monomeric aromatic diisocyanates and their polymers. Typical aliphatic diisocyanates include hexamethylene diisocyanate, isophorone diisocyanate and hydrogenated diphenylmethane diisocyanate. Typical aromatic isocyanates include toluene diisocyanates and biphenylmethane diisocyanates.

The plastics material such as a thermoset resin may be useful for parts in boat hulls, baths, shower trays, seats, conduits and bulkheads for trains, trams, ships aircraft, body panels for automotive vehicles and truck beds.

In one embodiment, thermoplastic resins include polyolefins, polyesters, polyamides, polycarbonates, polyurethanes, polystyrenics, poly(meth)acrylates, celluloses and cellulose derivatives. Said compositions may be prepared in a number of ways but melt mixing and dry solid blending are typical methods. Examples of a suitable thermoplastic include (low density, or linear low density or high density) polyethylene, polypropylene, polystyrene, polyethylene terephthalate (PET), polybutylene terephthalate (PBT), nylon 6, nylon 6/6, nylon 4/6, nylon 6/12, nylon and nylon 12, polymethylmethacrylate, polyethersulphone, polysulphones, polycarbonate, polyvinyl chloride (PVC), thermoplastic polyurethane, ethylene vinyl acetate (EVA), Victrex PEEK™ polymers (such as oxy-1,4-phenylenoeoxy-1,4-phenylenecarbonyl-1,4-phenylene polymers) and acrylonitrile butadiene styrene polymers (ABS); and various other polymeric blends or alloys.

If desired, the compositions containing plastic material may contain other ingredients, for example, dispersants other than the compound of the present invention, antifogging agents, nucleators, blowing agents, flame retardants, process aids, surfactants, plasticisers, heat stabilizers, UV absorbers, anti-oxidants, fragrances, mould release aids, anti-static agents, anti-microbial agents, biocides, coupling agents, lubricants (external and internal), impact modifiers, slip agents, air release agents and viscosity depressants.

The compositions typically contain from 1 to 95% by weight of the particulate solid, the precise quantity depending on the nature of the solid and the quantity depending on the nature of the solid and the relative densities of the solid and the polar organic liquid. For example, a composition in which the solid is an organic material, such as an organic pigment, in one embodiment contains from 15 to 60% by weight of the solid whereas a composition in which the solid is an inorganic material, such as an inorganic pigment, filler or extender, in one embodiment contains from 40 to 90% by weight of the solid based on the total weight of composition.

The composition may be prepared by any of the conventional methods known for preparing dispersions. Thus, the solid, the organic medium and the dispersant may be mixed in any order, the mixture then being subjected to a mechanical treatment to reduce the particles of the solid to an appropriate size, for example, by ball milling, bead milling, gravel milling, high shear mixing or plastic milling until the dispersion is formed. Alternatively, the solid may be treated to reduce its particle size independently or in admixture with either, the organic medium or the dispersant, the other ingredient or ingredients then being added and the mixture being agitated to provide the composition.

In one embodiment, the composition of the present invention is suited to liquid dispersions. In one embodiment, such dispersion compositions comprise: (a) 0.5 to 40 parts of a particulate solid, (b) 0.5 to 30 parts of a composition as disclosed herein above, and (c) 30 to 99 parts of an organic medium; wherein all parts are by weight and the amounts (a)+(b)+(c)=100.

In one embodiment, component a) includes 0.5 to 40 parts of a pigment and such dispersions are useful as mill-bases, coatings, paints, toners, or inks.

If a composition is required including a particulate solid and a composition as disclosed herein above in dry form, the organic liquid is typically volatile so that it may be readily removed from the particulate solid by a simple separation means such as evaporation. In one embodiment, the composition includes the organic liquid.

If the dry composition consists essentially of the composition as disclosed herein above and the particulate solid, it typically contains at least 0.2%, at least 0.5% or at least 1.0% the composition as disclosed herein above based on weight of the particulate solid. In one embodiment, the dry composition contains not greater than 100%, not greater than 50%, not greater than 20%, or not greater than 10% by weight of the composition as disclosed herein above based on the weight of the particulate solid. In one embodiment, the composition, as disclosed herein above, is present at 0.6 wt. % to 8 wt. %.

As disclosed hereinbefore, the compositions of the invention are suitable for preparing mill-bases wherein the particulate solid is milled in an organic liquid in the presence of a composition, as disclosed herein above, or salts thereof.

Thus, according to a still further embodiment of the invention, there is provided a mill-base including a particulate solid, an organic liquid and a composition as disclosed herein above, or salts thereof.

Typically, the mill-base contains from 20 to 70% by weight particulate solid based on the total weight of the mill-base. In one embodiment, the particulate solid is not less than 10 or not less than 20% by weight of the mill-base. Such mill-bases may optionally contain a binder added either before or after milling. The binder is a polymeric material capable of binding the composition on volatilisation of the organic liquid.

Binders are polymeric materials including natural and synthetic materials. In one embodiment, binders include poly(meth)acrylates, polystyrenics, polyesters, polyurethanes, alkyds, polysaccharides such as cellulose, and natural proteins such as casein. In one embodiment, the binder is present in the composition at more than 100% based on the amount of particulate solid, more than 200%, more than 300% or more than 400%.

The amount of optional binder in the mill-base can vary over wide limits but is typically not less than 10%, and often not less than 20% by weight of the continuous/liquid phase of the mill-base. In one embodiment, the amount of binder is not greater than 50% or not greater than 40% by weight of the continuous/liquid phase of the mill-base.

The amount of dispersant in the mill-base is dependent on the amount of particulate solid, but is typically from 0.5 to 5% by weight of the mill-base. Continuous/liquid phase includes all of the liquid materials (e.g., solvent, liquid binder, dispersants, etc.) and any solid material that dissolves in the liquid materials after a short mixing period, e.g., it specifically excludes solid particulates that are dispersed in the continuous liquid phase.

Dispersions and mill-bases made from the composition of the invention are particularly suitable for use in aqueous, non-aqueous and solvent free formulations in which energy curable systems (ultra-violet, laser light, infra-red, cationic, electron beam, microwave) are employed with monomers, oligomers, etc., or a combination present in the formulation. They are particularly suitable for use in coatings such as paints, varnishes, inks, other coating materials and plastics. Suitable examples include their use in low, medium and high solids paints, general industrial paints including baking, 2 component and metal coating paints such as coil and can coatings, powder coatings, UV-curable coatings, wood varnishes; inks, such as flexographic, gravure, offset, lithographic, letterpress or relief, screen printing and printing inks for packaging printing, non impact inks such as ink jet inks, inks for ink jet printers and print varnishes such as overprint varnishes; polyol and plastisol dispersions; non-aqueous ceramic processes, especially tape-casting, gel-casting, doctor-blade, extrusion and injection moulding type processes, a further example would be in the preparation of dry ceramic powders for isostatic pressing; composites such as sheet moulding and bulk moulding compounds, resin transfer moulding, pultrusion, hand-lay-up and spray-lay-up processes, matched die moulding; construction materials like casting resins, cosmetics, personal care like nail coatings, sunscreens, adhesives, toners, plastics materials and electronic materials, such as coating formulations for colour filter systems in displays including OLED devices, liquid crystal displays and electrophoretic displays, glass coatings including optical fibre coatings, reflective coatings or anti-reflective coatings, conductive and magnetic inks and coatings. They are useful in the surface modification of pigments and fillers to improve the dispersibility of dry powders used in the above applications. Further examples of coating materials are given in Bodo Muller, Ulrich Poth, Lackformulierung und Lackrezeptur, Lehrbuch fr Ausbildung und Praxis, Vincentz Verlag, Hanover (2003) and in P. G. Garrat, Strahlenhartung, Vincentz Verlag, Hanover (1996). Examples of printing ink formulations are given in E. W. Flick, Printing Ink and Overprint Varnish Formulations—Recent Developments, Noyes Publications, Park Ridge N.J., (1990) and subsequent editions.

In one embodiment, the composition of the invention further includes one or more additional known dispersants.

The following examples provide illustrations of the invention. These examples are non exhaustive and are not intended to limit the scope of the invention.

EXAMPLES

Inventive Compound 1 (IC1): 12-hydroxystearic acid (404.3 g) is placed postionwise in a 1 L flask with heating until the acid melted. The flask is attached to a Dean Stark apparatus with a stirrer. The mixture is then heated to 110° C. under $N_2$ with stirring (at 230 rpm). The product of EX1 (as described above) (44.7 g) is then added portion wise through a powder funnel over 5 minutes. The reaction is then heated to 150° C. and held for 4 hours. 4.7 g of water is collected. The flask is cooled to 100° C. and the zirconium butoxide (80% solution) (2.6 g) is added via a pipette. A subsurface nitrogen sparge was added and set to 471.94 $cm^3$/min (or 1 scfh). The reaction is heated to 195° C. and held for 22 hours. Water (8.3 g) is collected. The reaction is cooled and diluent oil is added (150.3 g). The resultant mixture is stirred for 1 hour. A further 147.2 g of diluent oil is added to homogenise for a further 30 minutes at 100° C. The product is then filtered through Fax-5 diatomaceous filter. A further 200 g of diluent oil is added to homogenise for a further 30 minutes at 100° C. to give the final product.

Inventive Compound 2 (IC2): 12-hydroxystearic acid (400.9 g) is placed postionwise in a 1 L flask with heating until the acid melted. The flask is attached to a Dean Stark apparatus with a stirrer. The mixture is then heated to 110° C. under $N_2$ with stirring (at 240 rpm). 40.6 g of 4-aminodiphenylamine is then added portion wise through a powder funnel over 5 minutes. The reaction is then heated to 150° C. and held for 4 hours. The flask is cooled to 100° C. and the zirconium butoxide (80% solution) (2.5 g) is added via a pippette. A subsurface nitrogen sparge was added and set to 471.94 $cm^3$/min (or 1 scfh). The reaction is heated to 195° C. and held for 22 hours. The reaction is cooled to 100° C. and diluent oil is added (133.5 g). The resultant mixture is stirred for 1 hour at 100° C. The product is then filtered through Fax-5 diatomaceous filter to give the final product.

Inventive Compound 3 (IC3): Ricinoleic acid (631.5 g) is placed postionwise in a 1 L flask with heating until the acid melted. The flask is attached to a Dean Stark apparatus with a stirrer. The mixture is then heated to 110° C. under $N_2$ with stirring (at 200 rpm). 69.1 g of the product of EX1 described above is then added portion wise through a powder funnel over 10 minutes. The reaction is then heated to 150° C. and held for 4 hours. 14 g of water is collected. The flask is cooled to 100° C. and the zirconium butoxide (80% solution) (4.0 g) is added via a pippette. A subsurface nitrogen sparge was added and set to 471.94 $cm^3$/min (or 1 scfh). The reaction is heated to 195° C. and held for 19 hours. Water (23.3 g) is collected. The reaction is cooled to 100° C. and diluent oil is added (220.3 g). The resultant mixture is stirred for 1 hour at 100° C. The product is then filtered through Fax-5 diatomaceous filter to give the final product.

Inventive Compound 4 (IC4): Ricinoleic acid (406 g; 1.362 moles) and the product of EX1 (89.6 g; 0.2357 moles) are charged to a 1 liter flask, under a nitrogen sparge. The flask is attached to a Dean Stark apparatus with a stirrer. The flask is heated to 150° C. and maintained at this temperature for 5 hours. Zirconium butoxide (2.5 g) is then charged and the batch heated to 195° C. for 20 hours. The product is then cooled.

Inventive Compound 5 (IC5): Ricinoleic acid (516.6 g; 1.734 moles) and the product of EX1 (44.7 g; 0.1176 moles) are charged to a 1 liter flask, under a nitrogen sparge. The flask is attached to a Dean Stark apparatus with a stirrer. The flask is heated to 150° C. and maintained at this temperature for 5 hours. Zirconium butoxide (2.5 g) is then charged and the batch heated to 195° C. for 20 hours. The product is then cooled.

Inventive Compound 6 (IC6): 12-Hydroxystearic acid (405.6 g; 1.352 moles) is melted out at 100° C. in a 1 liter flask, under a nitrogen sparge. The flask is attached to a Dean Stark apparatus with a stirrer. Once the 12-hydroxystearic acid, the flask is charged with melted the product of EX1 (89.6 g; 0.2379 moles). The flask is heated to 150° C. and maintained at this temperature for 5 hours. Zirconium butoxide (2.5 g) is then charged and the batch heated to 195° C. for 20 hours. The product is then cooled.

Inventive Compound 7 (IC7): 12-Hydroxystearic acid (515.6 g; 1.719 moles) is melted out at 100° C. in a 1 liter flask, under a nitrogen sparge. The flask is attached to a Dean Stark apparatus with a stirrer. Once the 12-hydroxystearic acid, the flask is charged with melted the product of EX1 (44.7 g; 0.2379 moles). The flask is heated to 150° C. and maintained at this temperature for 5 hours. Zirconium butoxide (2.5 g) is then charged and the batch heated to 195° C. for 20 hours. The product is then cooled.

Inventive Compound 8 (IC8): Polyisobutylenesuccinic anhydride (250.5 g; 0.2386 moles) and the product of EX1 (89.6 g; 0.2357 moles) are charged to a 1 liter flask, under a nitrogen sparge. The flask is attached to a Dean Stark apparatus with a stirrer. The flask is heated to 160° C. and maintained at this temperature for 8 hours. The flask is then heated to 180° C. and held at for 5 hours. The product is then cooled.

Comparative Example 1

(CE1) is a dispersant as described in Example 2 of GB 1 373 660.

Comparative Example 2

(CE2) is a dispersant as described in Example 5 of U.S. Pat. No. 4,224,212.

0.38 g of each of the compounds of the invention and comparative examples are each dissolved in toluene (6.47 g) by warming as necessary and added to a trident vial. 0.15 g of Solsperse®5000 (ex., The Lubrizol Corporation) is added. 17 g of 3 mm diameter glass beads and 3 g of copper phthalocyanine pigment (Monastral Blue BG, ex Heubach) is added. The vial is capped and sealed. A control vial is also prepared that does not contain a dispersant. The pigment is milled by shaking on a horizontal shaker for 16 hours. The viscosity of the resulting dispersion is assessed using an arbitrary scale of A to E (good to poor) based on stability of dispersion upon standing. The results obtained are as follows:

| Compound | Rating |
| --- | --- |
| IC1 | A |
| IC2 | B |
| IC3 | A |
| IC4 | A |
| IC5 | A |
| IC6 | A |
| IC7 | A |
| IC8 | B |
| CE1 | B/C |
| CE2 | C |
| Control | E |

The results indicate that the compounds of the invention provide superior fluidity of pigment dispersions in a non-polar organic medium.

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil, which may be customarily present in the commercial material, unless otherwise indicated. It is to be understood that the upper and lower amount, range, and ratio limits, set forth herein, may be independently combined. Similarly, the ranges and amounts for each element of the invention may be used together with ranges or amounts for any of the other elements.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A compound obtained by reacting an aromatic amine with a hydrocarbyl-substituted acylating agent, wherein the hydrocarbyl-substituted acylating agent is selected from the group consisting of a $C_{10-30}$-hydrocarbyl substituted acylating agent, an oligomer or polymer from condensation polymerisation of a hydroxy-substituted $C_{10-30}$ carboxylic acid into a polyester, and an optionally hydroxy-substituted $C_{10-30}$ carboxylic acid, or mixtures thereof, wherein the aromatic amine is represented by the Formula (1a):

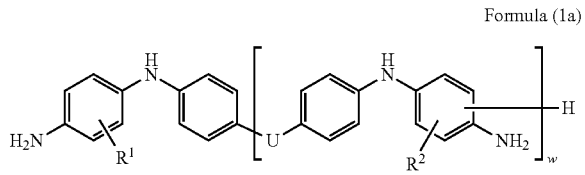

Formula (1a)

wherein independently each variable,
$R^1$ is hydrogen or a $C_{1-5}$ alkyl group;
$R^2$ is hydrogen or a $C_{1-5}$ alkyl group;
U is an aliphatic, alicyclic or aromatic group, with the proviso that when U is aliphatic, the aliphatic group may be linear or branched alkylene group containing 1 to 5 carbon atoms; and w is 1 to 10.

2. The compound of claim 1, wherein the aromatic amine to hydrocarbyl-substituted acylating agent mole ratio may be in the range of 2:1 to 1:10.

3. The compound of claim 1, wherein the aromatic amine to hydrocarbyl-substituted acylating agent mole ratio may be 1:1 to 1:2.

4. The compound of claim 1, wherein the compound is obtained by reacting an aromatic amine with a $C_{10-30}$-hydrocarbyl substituted acylating agent, or mixtures thereof, wherein the $C_{10-30}$-hydrocarbyl substituted acylating agent is an alk(en)yl-substituted succinic acid, anhydride, or partial esters thereof.

5. The compound of claim 4, wherein the $C_{10-30}$-hydrocarbyl substituted acylating agent is hexadecyl succinic anhydride, or mixtures thereof.

6. The compound of claim 1, wherein the hydrocarbyl-substituted acylating agent is a polyisobutylene succinic anhydride.

7. The compound of claim 6, wherein the polyisobutylene from which the polyisobutylene succinic anhydride is derivable has a number average molecular weight of 300 to 5000.

8. The compound of claim 6, wherein the polyisobutylene from which the polyisobutylene succinic anhydride is derivable has a number average molecular weight of 550 to 2500.

9. The compound of claim 6, wherein the polyisobutylene from which the polyisobutylene succinic anhydride is derivable has a number average molecular weight of 750 to 1000.

10. The compound of claim 6, wherein the polyisobutylene from which the polyisobutylene succinic anhydride is derivable has a number average molecular weight of 1600 to 2300.

* * * * *